US007107818B2

(12) United States Patent
Zilioli et al.

(10) Patent No.: US 7,107,818 B2
(45) Date of Patent: Sep. 19, 2006

(54) METHOD AND DEVICE FOR COMPREHENSIVE TWO-DIMENSIONAL GAS CHROMATOGRAPHY

(75) Inventors: Giacinto Zilioli, Cernusco sul Naviglio (IT); Jan Beens, TA Castricum (NL)

(73) Assignee: Thermo Electron S.p.A., Rodano (IT)

( * ) Notice: Subject to any disclaimer, the term of this patent is extended or adjusted under 35 U.S.C. 154(b) by 137 days.

(21) Appl. No.: 10/466,812

(22) PCT Filed: Feb. 4, 2003

(86) PCT No.: PCT/IT02/00062

§ 371 (c)(1),
(2), (4) Date: Nov. 6, 2003

(87) PCT Pub. No.: WO03/067250

PCT Pub. Date: Aug. 14, 2003

(65) Prior Publication Data

US 2004/0149010 A1 Aug. 5, 2004

(51) Int. Cl.
*G01N 30/02* (2006.01)
*B01D 53/02* (2006.01)

(52) U.S. Cl. .................. 73/23.41; 73/23.35; 73/23.37; 73/23.4; 95/86; 96/101

(58) Field of Classification Search .................. 73/41, 73/23.35; 422/86, 89, 60, 80; 96/101
See application file for complete search history.

(56) References Cited

U.S. PATENT DOCUMENTS 3,700,890 A * 10/1972 Kruezer .................. 250/341.1
5,135,549 A * 8/1992 Phillips et al. .................... 95/8
5,196,039 A * 3/1993 Phillips et al. .............. 210/656
5,398,539 A * 3/1995 Gordon et al. ............. 73/23.35
5,398,593 A * 3/1995 Sirkis ........................... 89/174
5,763,283 A * 6/1998 Cernosek et al. .......... 73/19.03

(Continued)

FOREIGN PATENT DOCUMENTS

EP        0 637 748 A    2/1995

(Continued)

OTHER PUBLICATIONS

Ledford et al. "J. High Resol. Chromatogr.", vol. 23, Mar. 2000, p. 202-204.*

(Continued)

*Primary Examiner*—Hezron Williams
*Assistant Examiner*—Ryan Christensen
(74) *Attorney, Agent, or Firm*—Nixon & Vanderhye (57) ABSTRACT

A method for detecting substances or mixtures of substances within a sample in an apparatus for comprehensive two-dimensional gas-chromatographic analysis according to the present invention, comprising the steps of:
  subjecting the sample to a first separation within a first capillary column;
  modulating in time the effluents from the first column by means of the subdivision into adjacent fractions of the effluents from the first column and subsequently sending each fraction into a second capillary column, the modulation of the effluents being periodic with a first modulation frequency $f_1$ of the sample;
  separating each of the fractions in the aforesaid second capillary column; and
  detecting, at the end of the second capillary column, the effluents by means of periodic sampling by discrete time points at a second frequency $f_2$.

The method moreover envisages the step of generating the first frequency $f_1$ of modulation and the second frequency $f_2$ of sampling in such a way that sampling by discrete points downstream of the second column will be in phase with the modulation of the effluents from the first column.

18 Claims, 4 Drawing Sheets

U.S. PATENT DOCUMENTS 5,929,321 A * 7/1999 Bertrand ............... 73/23.39
6,632,268 B1 * 10/2003 Seeley .................... 95/86
2001/0037727 A1 * 11/2001 Ledford et al. ........... 95/87

FOREIGN PATENT DOCUMENTS

WO           01/51179 A    7/2001

OTHER PUBLICATIONS

Phillips et al; "Comprehensive Two-Dimensional Gas Chromatograpy: A Hypenated Method with Strong Coupling Between the Two Dimensions"; Journal of Chromatography A, Elsevier Science, NL, vol. 856, No. 1-2, Sep. 24, 1999, pp. 331-347, XP004180086.

Ledford et al., "J. High Resol. Chromatogr.", vol. 23, Mar. 2000, p. 202-204.

* cited by examiner

1D-GC chromatogram (at the end of the 1st column)

Modulation

②

Raw 2D-GC chromatograms (at the end of the 2nd column)

Transformation

③

2nd dimension chromatogr stacked side by side

Visualisation

④

Contour plot

METHOD AND DEVICE FOR COMPREHENSIVE TWO-DIMENSIONAL GAS CHROMATOGRAPHY

This application is the US national phase of international application PCT/IT02/00062 filed 04 Feb. 2003, which designated the US.

TECHNICAL FIELD

The present invention relates to a method for detecting substances or mixtures of substances contained in a sample by means of an apparatus for comprehensive two-dimensional gas-chromatographic analysis.

BACKGROUND OF THE INVENTION

Comprehensive two-dimensional gas-chromatographic analysis, also referred to as GC×GC (or else as "comprehensive 2D GC"), is a recent technique of analysis that involves subjecting the sample to be analysed to a first separation in a traditional capillary column and then injecting all the gaseous effluents of the first column, appropriately focused (concentrated) in fractions of predefined size, into a second capillary column having characteristics, and hence capacity of analytical detection, different from the first capillary column.

GC×GC analysis enables, thanks to fractionation (i.e. splitting in fractions) of the effluents of the first column and to the subsequent analysis of the fractions in the second column, a high analytical resolution that leads to a better and more sensitive identification of the substances present in the sample analysed.

In greater detail, the method of GC×GC analysis leads to a separation of the sample in a first capillary column and a further separation of the effluents of the first column, appropriately modulated, in a second column set in series to the first. All the effluents of the first column are subjected to a periodic modulation in time that consists in their subdivision and focusing in adjacent fractions having a constant extension in time by means of modulators (for example, thermal modulators) in which the effluents from the first column are first slowed down (focusing) and then accelerated again for introduction into the second column. Each fraction of the effluents thus modulated, i.e., each gas pulse, is then sent into the second capillary column so as to be further separated and analysed by a detector set in a position corresponding to the output section of the said second capillary column.

To guarantee the continuity of the analysis, the second capillary column is a column of a fast type, i.e., shorter and with a smaller diameter than the first capillary column, and the focused fractions of the effluents from the first column have extremely small time dimensions (<100 ms), thanks to the choice of an appropriate frequency of modulation of the said effluents.

The results of GC×GC analysis may be viewed by means of a three-dimensional Cartesian chromatogram, or by means of a contour plot (i.e. a level-curve graph), that presents two temporal axes (or time dimensions), one for each dimension of the analysis, and one axis (or level curve) along which there appears the intensity of the signal at output from the detector downstream of the second column. The peaks in the chromatogram, the height of which is proportional to the intensity of the signal at output from the corresponding detector and the position of which along each axis is a function of the instant of outflow (and hence of volatility) from the column considered of the substance or mixture at output, indicate the presence of a certain substance or mixture of substances.

In particular, the chromatogram is obtained as follows: each effluent, generated by the separation of the sample, can be detected, together with the instant of outflow, at output from the first capillary column, giving rise to a peak of height proportional to its quantity. This technique is the one usually adopted in one-dimensional gas chromatography. The effluents from the first column are then modulated in adjacent fractions, as described above, and each fraction is sent into the second capillary column, where it undergoes a further separation. Downstream of the second capillary column, the effluents from the latter are detected, together with the instant of output, giving rise to a series of peaks of restricted dimensions proportional to the size of each substance or mixture further separated in the second column.

The detection of the peaks at output from the second capillary column, which is obtained via discrete sampling, forms a continuous time series of digital signals in time proportional to the effluents from the second capillary column. To create the chromatogram, the continuous series of digital signals must be subdivided into a plurality of subsets ("cuts" or bands) of constant time dimension (and hence of equal number given by the discrete acquisition of the peaks), in such a way that their ordering side-by-side will give rise to a matrix in which one axis indicates the number of signals (points) acquired of the chromatogram of the second dimension and the other axis indicates the number of chromatograms of the second dimension.

Given that the number of bands (or subdivisions) of the second dimension, corresponding, that is, to the second capillary column, must be equal to the number of fractions of the effluents from the first column, the dimension of each subset, and hence the time interval of each subdivision, must therefore theoretically have the same time dimension as each fraction modulated at output from the first capillary column.

In other words, the amplitude of each modulation interval should theoretically coincide with the amplitude of each subset that divides the continuous time series of digital signals acquired.

However, the periodic modulation of the effluents from the first column takes place with a frequency that is determined beforehand on the basis of the characteristics of the first and second columns, whilst the acquisition by discrete points (sampling) of the peaks detectable downstream of the second column is obtained with a frequency of its own of the detector.

This means that the number of points, which are equidistant in time, acquired by the detector downstream of the second capillary column cannot be, and usually is not, perfectly contained in the time interval of modulation of the effluents from the first column, and this leads to a time drift in the acquisition of these points. If, for example, the time interval of each modulation is equal to 50 ms (20 Hz) and the acquisition of the sampling points is obtained every 0.3 ms (3.33 MHz), the number of sampling points in each modulation interval will be equal to 166, but there will be a time deviation equal to 0.2 ms, which will lead to an offset (out-of-phase) equal to 0.1 ms in the acquisition of the first sampling point and of the $166^{th}$ sampling point of the subsequent modulation interval and which, in the third subsequent modulation interval, will lead to an offset in the start of sampling, whereby the $166^{th}$ sampling point will coincide with the instant of start of the fourth modulation interval, and thus a sampling point will be lost in the third interval and so forth (the so-called "leap-year effect"). This situation, which is linked to the offset between the intervals of modulation and acquisition of the data downstream of the second capillary column, generates a time drift in the data acquired, and hence in the positions of the peaks detected in time that frequently renders any interpretation thereof difficult, if not indeed impossible.

Figure 1A:
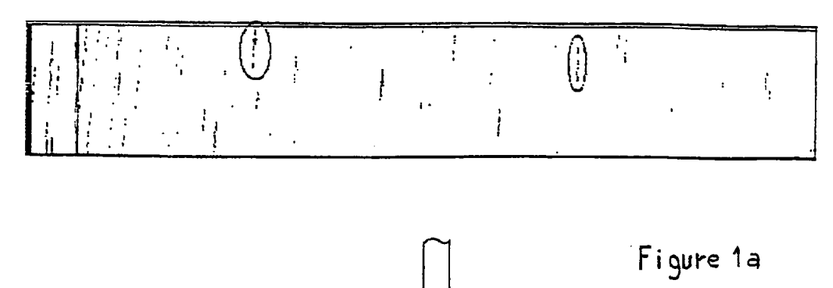
FIGS. 1a, 1b are two level-curve chromatograms in schematic form of the same sample obtained (1a) with the technique of synchronization of the modulation/acquisition of the data according to the present invention, and (1b) with the current technique in which there is no synchronization between the frequencies of modulation and of acquisition.
Figure 1B:
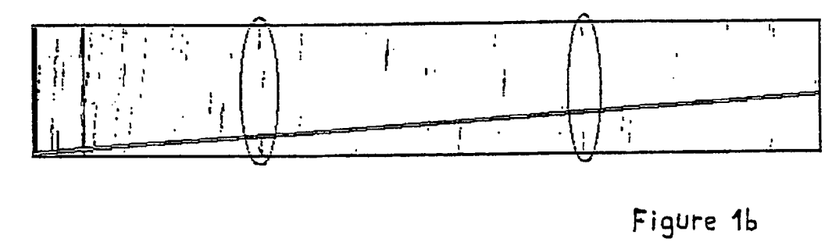

An example of this time drift in the sampling is given in FIG. 1b, in which the axis of the sampling times is inclined as a result of the offset referred to above.

The U.S. Pat. No. 5,135,549 in the name of Phillips and Liu proposes synchronizing the start of the modulation of the effluents from the first column with the start of the acquisition of the data, when the detector downstream of the second column is of the scanning type, such as, for example, a mass spectrometer. This technique, albeit reiterated at each modulation pulse of the sample, does not solve the problem of the offset between acquisition frequency and modulation frequency and furthermore presupposes that the detection device presents an initial transient zero and will enable a frequent re-initialization of the detection.

A purpose of the present invention is to provide a method for detecting substances or mixtures of substances within a sample in an apparatus for comprehensive two-dimensional gas-chromatographic analysis (GC×GC) that does not present the drawbacks of the known art and that in particular will prevent the time drift of the data acquired on the corresponding chromatogram.

Another purpose of the present invention consists in providing a method of GC×GC analysis that will prove particularly precise and that does not require a continuous synchronization of the modulator and of the detector.

A further purpose of the present invention is that of providing an apparatus for comprehensive two-dimensional gas-chromatographic analysis (GC×GC) of the type comprising a first separation column, a second separation column, and a modulator of the effluents from the first separation column, which will yield chromatograms that are free from time drift and are extremely precise.

SUMMARY OF THE INVENTION

These and other purposes are achieved by the method according to the first independent claim and the subsequent four dependent claims and by the apparatus according to the sixth independent claim and the subsequent dependent claims regarding the apparatus.

The method for detecting substances or mixtures of substances within a sample in an apparatus for comprehensive two-dimensional gas-chromatographic analysis, according to the present invention, comprises the steps of:

subjecting the sample to a first separation within a first capillary column;

modulating in time the effluents from the first column by means of the subdivision into adjacent fractions of the effluents from the first column and the subsequent sending of each fraction into a second capillary column, the modulation of the effluents being periodic with a first modulation frequency $f_1$ of the sample;

separating each of the fractions in the aforesaid second capillary column; and detecting, at the end of the second capillary column, the effluents by means of periodic sampling by discrete time points at a second frequency $f_2$.

The method moreover involves the step of:

generating the first frequency $f_1$ of modulation and the second frequency $f_2$ of sampling in such a way that the sampling by discrete points downstream of the second column will be in phase with the modulation of the effluents from the first column.

According to a preferred aspect of the present invention, the frequency $f_1$ and the frequency $f_2$ are harmonics of different order of one and the same fundamental frequency f.

In a particular embodiment of the method according to the present invention, the method involves the step of generating the aforesaid first frequency $f_1$ of modulation and the aforesaid second frequency $f_2$ of sampling in such a way that $f_1$ and $f_2$ will be one the multiple of the other, or vice versa, and that they will be synchronized with each other, so that the sampling by discrete points will be in phase with the modulation of the effluents from the first column.

In addition, according to the present invention the apparatus for comprehensive two-dimensional gas-chromatographic analysis is of the type comprising a first separation column, a second separation column and a modulator of the effluents from the first separation column set in series between the first and the second column in order to obtain a modulation of the effluents from the first column at a first frequency $f_1$, and means for detecting the effluents from the second column by means of sampling by discrete points at a second frequency $f_2$. The apparatus comprises means for generating and/or synchronizing the first frequency $f_1$ of modulation and the second frequency $f_2$ of sampling in such a way that the sampling by discrete points will be in phase with said modulation of the effluents from said first column.

BRIEF DESCRIPTION OF THE DRAWINGS

There follows a description, purely by way of non-limiting example, of some preferred embodiments of the apparatus and of the method according to the present invention, with the aid of the annexed figures, in which.

PREFERRED MODE TO CARRY OUT THE INVENTION

Figure 2:
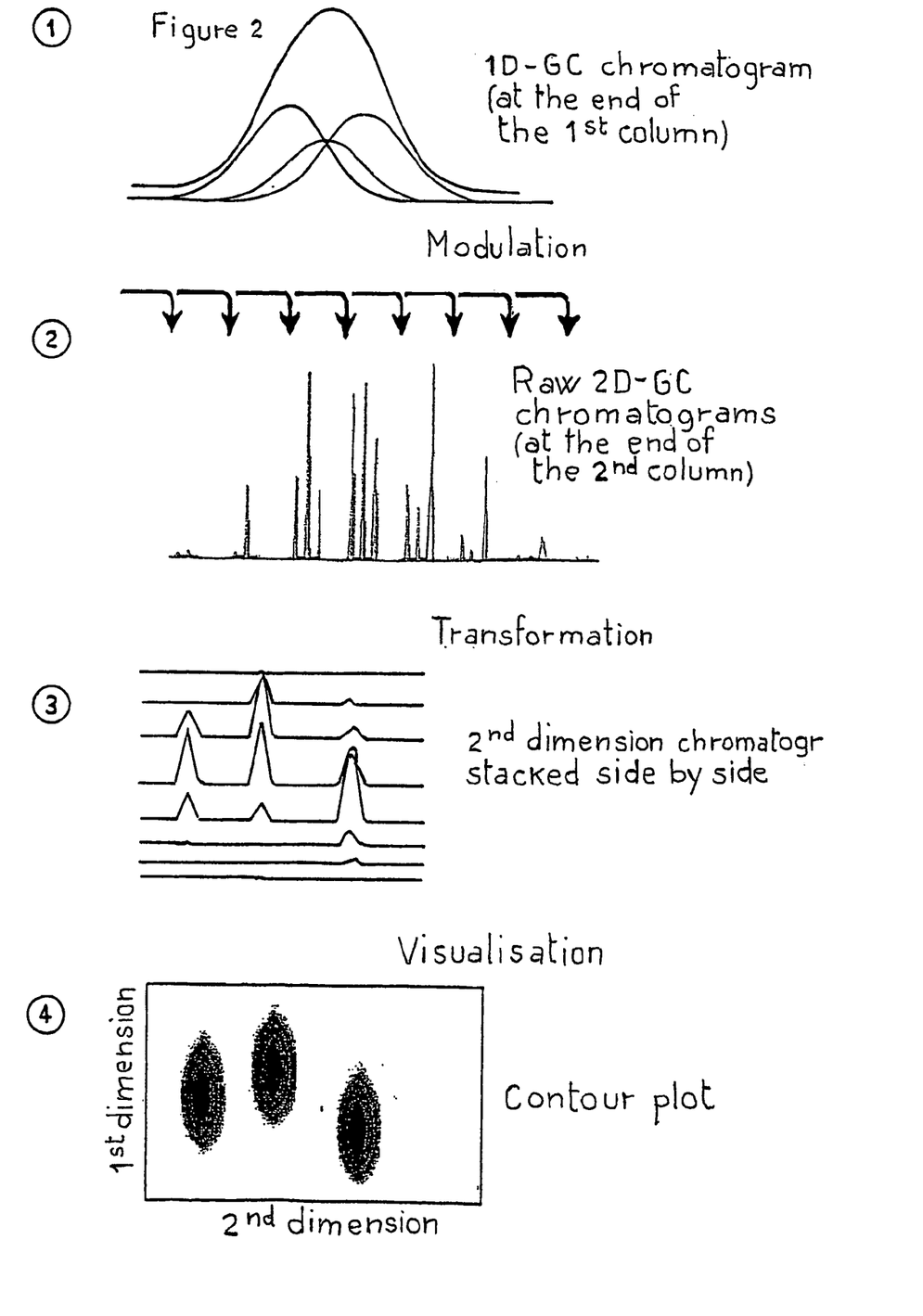
FIG. 2 is a diagram illustrating the steps for obtaining a chromatogram in an apparatus for GC×GC gas-chromatographic analysis.
Figure 5:
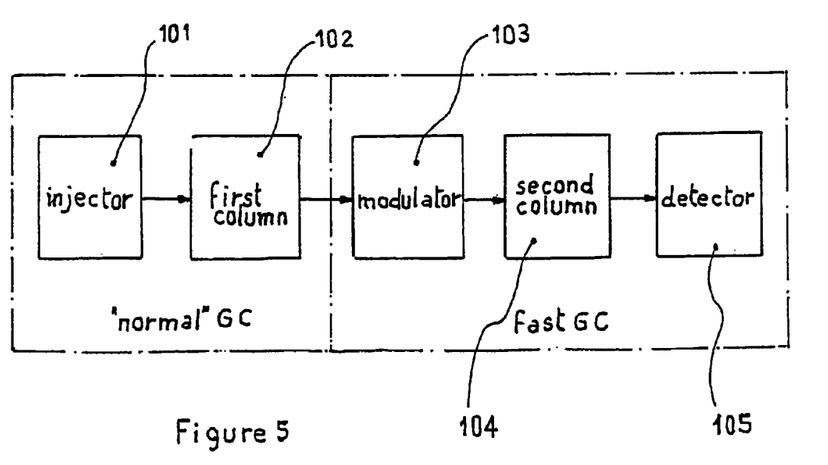
FIG. 5 is a diagram of an apparatus for GC×GC analysis.

With reference to FIGS. 2 and 5, there follows a brief description of a standard process of acquisition of the data corresponding to comprehensive two-dimensional gas-chromatographic analysis (GC×GC) of a generic sample.

The apparatus for the GC×GC analysis can be schematically represented as in FIG. 5 and comprises an injector 101 for introduction of the sample into a first capillary column 102 of a traditional type. Within the column 102, which is subjected to a certain thermal program and has a predefined stationary phase, a first separation of the sample is obtained. Downstream of the first capillary column 102, and in series with the latter, is set a modulator 103 that has the function of focusing (concentrating) the effluents from the first column 102 and of subdividing these effluents into fractions, on a constant time base, namely a constant frequency $f_1$. Each of the fractions with which the effluents from the column 102 are modulated are then sent into a second capillary column 104, usually of a "fast" type, which is shorter and of a smaller diameter as compared to the column 102, for a further separation of these fractions.

Finally, in a position corresponding to the output section of the second column 104 there is present a detector 105 which is capable of detecting, by means of sampling by discrete points, whatever flows out of said second column 104.

More in particular, from an examination also of FIG. 2, it may be noted that the output of the effluents from the first column 102, which is a consequence of the first separation of the sample within the latter, is able to generate, if detected, a traditional two-dimensional chromatogram (point (1) of the diagram of FIG. 2), which, for each effluent, presents a peak set at a precise instant in time from the start of the analysis having a given height. The instant of detection of the peak and its dimension are directly correlated to the substance, or mixture of substances coming out of the first column 102 and to the quantity of the substance or mixture of substances.

Each effluent, which is produced by the separation in the first capillary column 102, according to a technique of comprehensive 2D gas chromatography, is then modulated in the modulator 103, i.e., concentrated, and injected into the second capillary column 104. The modulation, which takes place with a frequency fi, can be carried out, according to the known art, by means of thermal or cryogenic modulators and has the purpose of enabling a further separation, in the second column 104, of each effluent from the first column. In brief, the effluents are fractionated by the modulator 103, at constant time intervals, and each adjacent fraction is sent into the second column 104, where it undergoes a further separation.

The effluents from the second column 104 are then detected by means, for example, of a traditional detector 105, such as a flame-ionization detector (F.I.D.), which periodically acquires, at a frequency $f_2$ of its own, a series of digital signals corresponding to what flows, in time, out of the second column. The set of data acquired, which is given on a time abscissa, gives rise to the diagram shown in point (2) of FIG. 2, in which each peak is proportional to the size of each effluent substance at output from the second column 104.

Given the modulation of the effluents from the first column, however, to obtain the correspondence between peaks of the second dimension (detected at output from the second column 104) and each fraction modulated downstream of the first capillary column 102, it is necessary to subdivide the signals obtained from the effluents of the first column 102 and then compose them, stacking them, on the axis of the second dimension of the graph that it is intended to obtain (see point (3) of FIG. 2). This subdivision must obviously be done at a point corresponding to each time interval of modulation of the effluents from the first column 102; i.e., it must follow the same frequency $f_1$ of modulation.

The data detected downstream of the second column 104 thus arranged, which may also be seen in a contour plot as shown in FIG. 2, point (4), provide extremely precise analytical indications.

The subdivision of the signals detected downstream of the second dimension with the modulation frequency $f_1$ can involve, in the prior art, as has been seen, the time drift of the peaks detected and a noticeable imprecision of detection.

In fact, with reference to FIGS. 1a and 1b, which represent a chromatogram corresponding to the analysis of one and the same sample that respectively does not present (FIG. 1a) and does present (FIG. 1b) this drift, the time interval A of each modulation (for which $f_1=1/A$) constitutes the time base of the subdivision, which, as described previously, is not usually synchronous with the time interval B (for which $f_2=1/B$) that elapses between one detection point and the subsequent one of the detector set downstream of the second column, for which the said time drift occurs. The peaks, which are circled in Figure 1a and belong to a fraction modulated downstream of the first column, are detected as belonging to two successive modulations in the chromatogram of FIG. 1b.

According to the present invention, this time drift of the chromatogram is avoided by synchronizing the time bases of the operation of modulation and of the acquisition of the data by the detector downstream of the second column; that is, by generating, respectively, the frequency $f_1$ of modulation and the frequency $f_2$ of sampling (discrete acquisition of the data) in such a way that the sampling by discrete points is in phase with the modulation of the effluents of the first column.

In particular, according to the invention, the said effect can be obtained by imposing the condition that the frequency $f_1$ of modulation and the frequency $f_2$ of sampling are frequencies of harmonic functions of the same order or of different order of one and the same fundamental harmonic.

In the case where the frequencies $f_1$ and $f_2$ were to coincide, and hence were to be frequencies of one and the same fundamental harmonic, these would obviously be synchronized.

In the case where the frequencies $f_1$ and $f_2$ were instead of harmonics of a different order, one of these could be the fundamental harmonic (i.e. of order 0).

According to a preferred aspect of the present invention, the method envisages that, to obtain modulation in phase with sampling, the aforesaid step of generating the frequencies of modulation ($f_1$) and sampling ($f_2$), comprises the steps of:

generating a basic frequency f;
generating the modulation frequency $f_1$, by dividing or multiplying the basic frequency f by a first integer $n_1$;
generating the sampling frequency $f_2$, by dividing or multiplying the basic frequency f by a second integer $n_2$; and
synchronizing the two frequencies $f_1$ and $f_2$, i.e., synchronizing the instant of start of modulation with sampling, or vice versa.

This method, in which $n_1$ and $n_2$ may be any positive integer (from 1 . . . N), is particularly suited to the purpose (see FIG. 3) in apparatus for GC×GC analysis equipped with an internal detector completely controlled by the apparatus.

Figure 3:
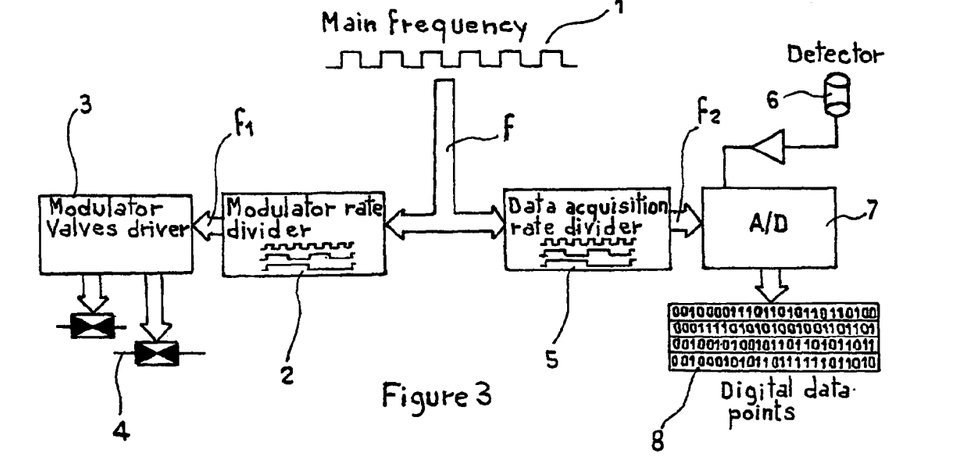
FIG. 3 is a diagram illustrating a preferred embodiment of an apparatus according to the present invention, in which the detector downstream of the second column is a traditional detector (for example, a flame-ionization detector—F.I.D.)

In this case, the apparatus comprises a generator 1 of a fundamental frequency f, a first frequency-divider device 2 for dividing the frequency f for generating a modulation frequency $f_1$, a device 3 for adjusting the modulation, operatively connected to the said frequency-divider device 2 and to the modulator 4.

The apparatus shown in the diagram further comprises a second frequency-divider device 5 for dividing the frequency f for generating a sampling frequency $f_2$, a control device 7 for controlling the detector 6, designed to control the latter on the basis of the frequency generated by the frequency-divider device 5 and to generate sampled points 8 acquired by said detector 6.

The apparatus illustrated, then, enables the frequencies $f_1$ and $f_2$, respectively of modulation and of sampling, to be obtained, synchronized in such a way that the modulation and the sampling, which are periodic operations, are in phase with one another.

This synchronization of the frequencies, which means that modulation and sampling are in phase, obviously prevents any time drift, in so far as the number of points sampled by the detector for each subdivision (corresponding to each modulation) of the raw time series of the data acquired is exactly an integer.

According to a further preferred embodiment of the present invention, in order to obtain modulation in phase with sampling, the method comprises the following steps:
generating said sampling frequency $f_2$;
generating said modulation frequency $f_1$ as a multiple or submultiple of said sampling frequency $f_2$; and
synchronizing the instant of start of modulation with sampling, or vice versa, i.e., synchronizing the frequencies $f_1$ and $f_2$.

The embodiment of the method referred to above finds particular application in apparatus for GC×GC analysis, in which the detector set downstream of the second capillary column is of the pulse type, such as, for example, a mass spectrometer.

In this case, the detector constitutes a device external to the gas-chromatographic apparatus, which operates according to a frequency $f_2$ of its own and, in order to guarantee that the periodic operation of modulation will be in phase with the periodic operation of acquisition of the data, it is necessary for the frequency $f_1$ to be modified so as to be rendered a multiple or submultiple of the frequency $f_2$ and thus be synchronized with the latter.

Figure 4:
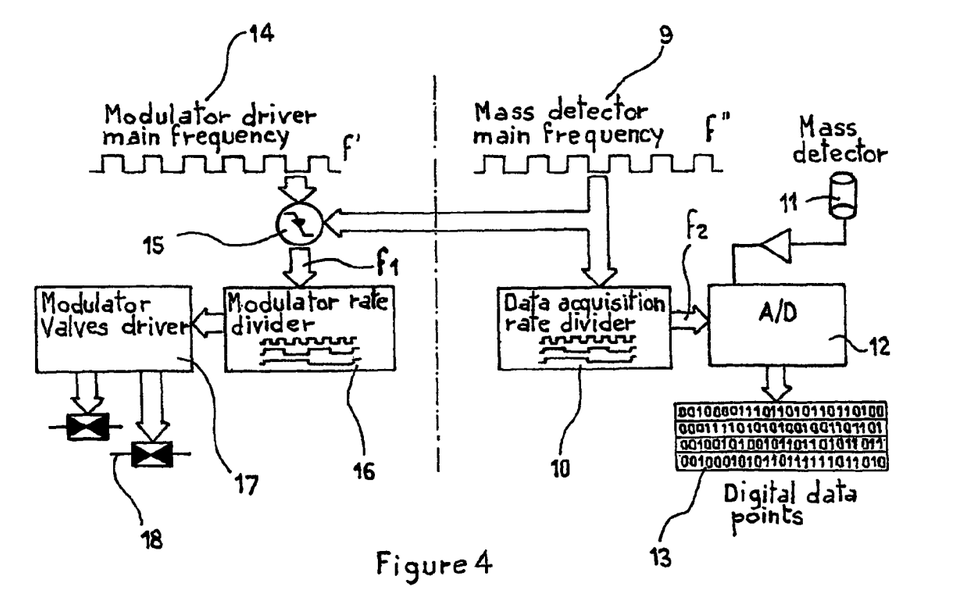
FIG. 4 is a diagram of another embodiment of an apparatus according to present invention, in which the method claimed is applied to an apparatus equipped with a mass spectrometer as detector downstream of the second column.

With reference to FIG. 4, the apparatus for GC×GC analysis illustrated thus comprises a detector 11 set downstream of the second capillary column of the pulse type, for example a mass spectrometer, a generator 9 of a fundamental frequency f'' for the detector, a frequency divider 10 for generating the sampling frequency $f_2$, and a device for digital acquisition of the data coming from the detector 11, operatively connected to the frequency divider 10 and designed for generating a continuous time series 13 of points sampled during detection of the effluents of the second capillary column. The apparatus illustrated further comprises a generator 14 of a fundamental frequency f' of modulation, a frequency divider 16 of this frequency f' into a modulation frequency $f_1$, and a control device 17 for controlling the modulation. The control device 17 is operatively connected to a modulator 18 and operates according to the frequency $f_1$. The apparatus further comprises a synchronizer $f_1$, which has the function of reading the frequency $f_2$ (or f'') coming from the detector and of controlling the divider 16 in such a way that the latter, on the basis also of the frequency f', will generate a frequency $f_1$ of modulation that will be a multiple or submultiple of the frequency $f_2$ or will be equal to the frequency $f_2$.

This guarantees that the modulation and the acquisition of the data will be in phase with one another and hence time drifts will not occur in the subsequent step of division of the series 13 into adjacent subdivisions.

It is of course envisaged that, according to a further embodiment of the present invention, in order to obtain the modulation in phase with the sampling, the method may comprise the following steps:
selecting and entering (performed by the user) a desired modulation frequency $f_1$;
generating said frequency $f_1$;
generating a sampling frequency $f_2$ that is a multiple or submultiple of the frequency $f_1$; and
synchronizing the instant of start of the modulation with sampling, i.e., synchronizing the frequencies $f_1$ and $f_2$.

In both of the embodiments described above, given that the modulation frequency $f_1$ can be chosen and set by the operator, for example on the basis of the type of second capillary column used, the apparatus illustrated can comprise means for approximating the frequency of modulation $f_1$ set or the sampling frequency $f_2$ in such a way that modulation and sampling are in phase and thus guarantee that an exact integer of points is acquired by the detector for each interval of subdivision (modulation) of the effluents from the first column.

EXPERIMENTAL EXAMPLE

Figure 6:
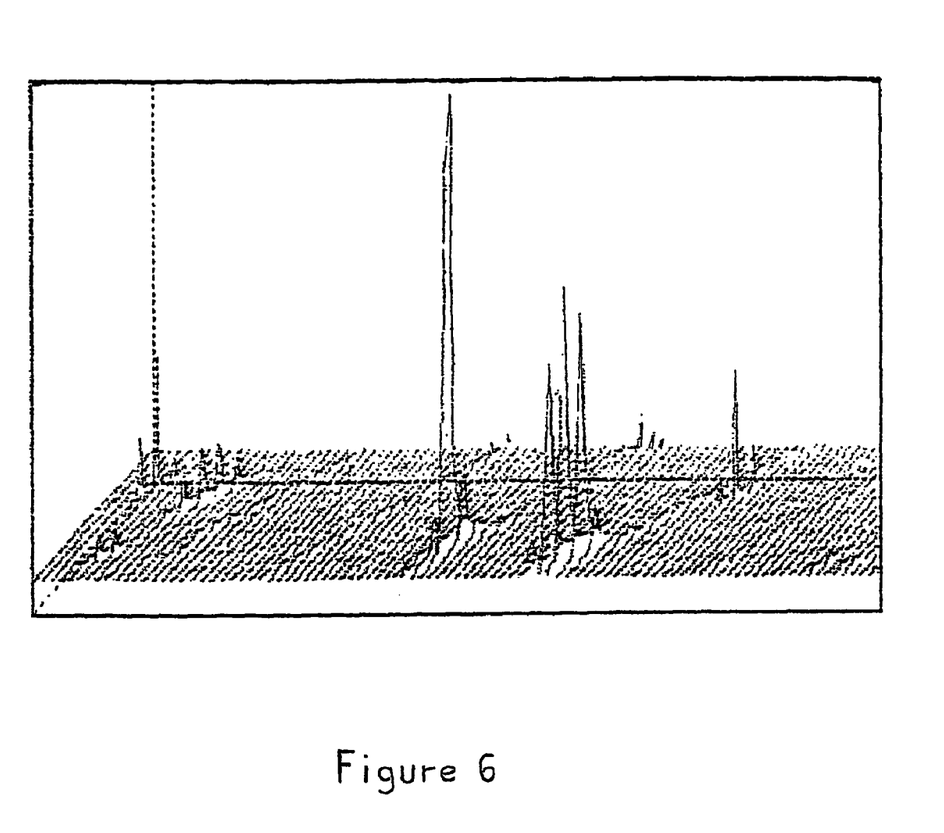
FIG. 6 is a 3D chromatogram obtained according to a preferred aspect of the method according to present invention.

In the embodiment illustrated in FIG. 3, the modulation is adjusted using a programming module that enables the operator to enter a time base ranging from 1 to 20 seconds (i.e., a modulation frequency $f_1$ between 0.05 Hz and 1 Hz). The apparatus is equipped with means for approximating the modulation frequency $f_2$ in such a way that the operations of modulation and sampling are in phase. Illustrated in FIG. 6 is a 3D chromatogram without time drift, generated starting from a total acquisition time of 4000 seconds, in which each modulation (subdivision of the effluents from the first column) is equal to an interval of 4 seconds (modulation frequency $f_1$ equal to 0.25 Hz) and in which the sampling frequency was set equal to $f_2$=100 Hz, i.e., the points acquired by the detector are set at a distance of 10 ms apart.

Consequently, 1000 subdivisions will be made on the time series of the data sampled, and each subdivision (or "band") will contain exactly 400 detection points. Synchronizing thus the two frequencies $f_1$ and $f_2$, in which $f_2$ is a multiple of order 400 of $f_1$, i.e., synchronizing the instant of start of the operations of modulation and sampling, we obtain the chromatogram illustrated, without any time drift.

The invention claimed is:

1. A method for detecting substances or mixtures of substances within a sample in an apparatus for comprehensive two-dimensional gas-chromatographic analysis, comprising the steps of:
subjecting the sample to a first separation within a first capillary column;
modulating in time the effluents from the first column by subdividing said effluents from the first column into adjacent fractions and by then sending each fraction into a second capillary column, said modulation of the effluents being periodic, with a first modulation frequency of the sample $f_1$;
separating each of the fractions in said second capillary column;
detecting, at the end of said second capillary column, the effluents by means of periodic sampling by discrete time points at a second frequency $f_2$; and generating said first frequency $f_1$ of modulation and said second frequency $f_2$ of sampling in such a way that said first frequency $f_1$ coincides with, or is a multiple or submultiple of, said second frequency $f_2$ and said sampling by discrete points will be in phase with said modulation of the effluents from said first column.

2. The method according to claim 1, wherein said frequency $f_1$ and said frequency $f_2$ are both frequencies of harmonics of different order of one and the same fundamental frequency.

3. The method according to claim 1, wherein said step of generating said frequencies $f_1$ and $f_2$ comprises the steps of:
generating a basic frequency f;
generating said modulation frequency $f_1$ by dividing or multiplying the basic frequency f by a first integer;
generating said sampling frequency $f_2$ by dividing or multiplying the basic frequency f by a second integer; and
synchronizing the instant of start of said modulation with said sampling, or, vice versa, the instant of start of said sampling with said modulation.

4. The method according to claim 1, wherein said step of generating said frequencies b and $f_2$ comprises the steps of:
generating said sampling frequency $f_2$;
generating said modulation frequency $f_1$ as a multiple or submultiple of said sampling frequency $f_1$; and
synchronizing the instant of start of said modulation with said sampling, or vice versa.

5. The method according to claim 1, further comprising the steps of:
selecting and entering a desired modulation frequency $f_1$;
generating said frequency $f_1$;
generating a sampling frequency $f_2$ that is a multiple or submultiple of said frequency $f_1$; and
synchronizing the instant of start of said modulation with said sampling, or vice versa.

6. An apparatus for comprehensive two-dimensional gas-chromatographic analysis of the type comprising a first separation column, a second separation column, a modulator of the effluents from the first separation column, which is set in series between said first column and said second column to obtain a modulation of said effluents at a first frequency $f_1$, and means for detecting the effluents from the second column by means of sampling by discrete points at a second frequency $f_2$, wherein the apparatus further comprises means for generating said first frequency $f_1$ of modulation and said second frequency $f_2$ of sampling in such a way that said first frequency $f_1$ coincides with, or is a multiple or submultiple of, said second frequency $f_2$ and said sampling by discrete points will be in phase with said modulation of the effluents from said first column.

7. The apparatus according to claim 6, wherein said synchronization means comprises a generator of a basic frequency f and at least one frequency divider of said basic frequency f for generating said frequency $f_1$ or said frequency $f_2$ as a multiple or submultiple of said basic frequency f.

8. The apparatus according to claim 7, further comprising two frequency dividers of said basic frequency f for generating both of said frequencies $f_1$ and $f_2$ as multiples or submultiples of said basic frequency f.

9. The apparatus according to claim 6, further comprising first means for generating a first frequency $f_1$ of modulation and second means for generating a second frequency $f_2$ of sampling, as well as a device for synchronizing said frequencies $f_1$ and $f_2$.

10. The apparatus according to claim 9, wherein said detecting means includes a predefined sampling frequency $f_2$ of its own, and wherein said modulator comprises a generator of modulation frequencies $f_1$ of its own, the apparatus comprising a device for synchronizing said frequency $f_1$ with respect to said frequency $f_2$.

11. The apparatus according to claim 10, in which said detection means includes a mass spectrometer set downstream of said second column.

12. The apparatus according to claim 9, wherein said means for generating said first frequency $f_1$ may be adjusted by a user for setting said frequency $f_1$.

13. An apparatus for comprehensive two-dimensional gas-chromatographic analysis comprising a first separation column, a second separation column, a modulator of effluents from the first separation column that is set in series between said first column and said second column to obtain a modulation of said effluents at a first frequency $f_1$, and a detector to detect the effluents from the second column via sampling by discrete points at a second frequency $f_2$, said apparatus being configured to generate said first frequency $f_1$ of modulation and said second frequency $f_2$ of sampling in such a way that said sampling by discrete points will be in phase with said modulation of the effluents from said first column, said aperture further comprising a generator of a basic frequency f and at least one frequency divider of said basic frequency f for generating said frequency $f_1$ or said frequency $f_2$ as a multiple or submultiple of said basic frequency f.

14. The apparatus according to claim 13, further comprising two frequency dividers of said basic frequency f for generating both of said frequencies $f_1$ and $f_2$ as multiples or submultiples of said basic frequency f.

15. An apparatus for comprehensive two-dimensional gas-chromatographic analysis comprising a first separation column, a second separation column, a modulator of effluents from the first separation column that is set in series between said first column and said second column to obtain a modulation of said effluents at a first frequency $f_1$, and a detector to detect effluents from the second column via sampling by discrete points at a second frequency $f_2$, wherein the apparatus is configured to generate said first frequency $f_1$ of modulation and said second frequency $f_2$ of sampling in such a way that said sampling by discrete points will be in phase with said modulation of the effluents from said first column, further comprising a first generator to generate said first frequency $f_1$ of modulation and a second generator to generate said second frequency $f_2$ of sampling, as well as a device to synchronize said frequencies $f_1$ and $f_2$.

16. The apparatus according to claim 15, wherein said detector includes a predefined sampling frequency $f_2$ of its own, and wherein said modulator comprises a generator of modulation frequencies $f_1$ of its own, the apparatus comprising a device for synchronizing said frequency $f_1$ with respect to said frequency $f_2$.

17. The apparatus according to claim 16, in which said detector includes a mass spectrometer set downstream of said second column.

18. The apparatus according to claim 15, wherein said first frequency $f_1$ may be adjusted by a user for setting said frequency $f_1$.

* * * * *